(12) United States Patent
Henderson et al.

(10) Patent No.: US 7,455,857 B2
(45) Date of Patent: Nov. 25, 2008

(54) ENERGY GENERATING COMPOSITION

(76) Inventors: Janeel Henderson, 15 S. Country La., Fruit Heights, UT (US) 84037; H. DeWayne Ashmead, 304 S. Mountain Rd., Fruit Heights, UT (US) 84037

( * ) Notice: Subject to any disclaimer, the term of this patent is extended or adjusted under 35 U.S.C. 154(b) by 776 days.

(21) Appl. No.: 10/410,588

(22) Filed: Apr. 8, 2003

(65) Prior Publication Data
US 2004/0204382 A1    Oct. 14, 2004

(51) Int. Cl.
*A61K 9/20*    (2006.01)
*A61K 9/00*    (2006.01)

(52) U.S. Cl. ........................ 424/464; 424/400
(58) Field of Classification Search .......... 424/464, 424/400
See application file for complete search history.

(56) References Cited

U.S. PATENT DOCUMENTS

| | | |
|---|---|---|
| 3,969,540 A * | 7/1976 | Jensen ..................... 426/657 |
| 4,020,158 A | 4/1977 | Ashmead et al. |
| 4,167,564 A | 9/1979 | Jensen |
| 4,216,143 A | 8/1980 | Ashmead |
| 4,216,144 A | 8/1980 | Ashmead |
| 4,599,152 A | 7/1986 | Ashmead |
| 4,725,427 A | 2/1988 | Ashmead et al. |
| 4,774,089 A | 9/1988 | Ashmead |
| 4,830,716 A | 5/1989 | Ashmead |
| 4,863,898 A | 9/1989 | Ashmead et al. |
| 5,292,538 A * | 3/1994 | Paul et al. ..................... 426/74 |
| 5,882,685 A | 3/1999 | Ashmead |
| 5,888,553 A | 3/1999 | Grant et al. |
| 6,114,379 A | 9/2000 | Wheelwright et al. |
| 6,132,724 A * | 10/2000 | Blum ........................ 424/725 |
| 6,451,341 B1 * | 9/2002 | Slaga et al. ................ 424/468 |
| 2003/0104076 A1 * | 6/2003 | Berkulin et al. ............ 424/725 |
| 2004/0071825 A1 * | 4/2004 | Lockwood .................. 426/72 |

* cited by examiner

*Primary Examiner*—Humera N Sheikh
(74) *Attorney, Agent, or Firm*—Thorpe North & Western LLP

(57) ABSTRACT

The present invention is drawn to an ephedra- and artificial stimulant-free energy promoting composition, comprising effective amounts of a magnesium amino acid chelate, a B vitamin, a pyruvate salt, and rhodiola. These ingredients work synergistically together to provide energy, without the use of artificial stimulants, caffeine, or ephedrine. Additional amino acid chelates can also be present, such as iron amino acid chelate, zinc amino acid chelate, copper amino acid chelate, manganese amino acid chelate, chromium amino acid chelate, and mixtures of second amino acid chelates.

20 Claims, No Drawings

ENERGY GENERATING COMPOSITION

FIELD OF THE INVENTION

The present invention is drawn to dietary supplement formulations that provide for the generation of energy, without the use of caffeine, ephedra, artificial stimulants, or other harmful chemicals, or drugs.

BACKGROUND OF THE INVENTION

Many harmful energy-producing substances that are used in nutritional supplements fall in the class of artificial stimulants. These substances, often times, can be addictive or otherwise harmful, particularly if abused. There are also many natural substances that can be harmful if abused as well. For example, caffeine and ephedrine or ephedra (ma huang) are natural substances that provide or enhance energy. Specifically, ephedrine, a thermogenic compound that burns brown fat near the kidneys and sternum, can be combined in diet or energy products with caffeine or other natural caffeine sources to provide a stimulant that is especially powerful.

Ephedrine is a stimulant that is used as an ingredient in diet pills, illegal recreational drugs, and legitimate over-the-counter medications to treat congestion and asthma. Ephedrine has a molecular structure similar to amphetamine. Ephedrine can produce adverse reactions, such as heart attack, stroke, tachycardia, paranoid psychosis, depression, convulsions, coma, fever, vomiting, palpitations, hypertension, and respiratory depression, particularly if abused or overused.

These side affects notwithstanding, some energy supplement manufacturers choose to use ephedrine in their energy formulations. As such, it would be desirable to provide an energy generating formulation that is ephedra free, as well as free of artificial ingredients, that provides noticeable energy enhancement to a user.

SUMMARY OF THE INVENTION

It has been recognized that it would be desirable to formulate an ephedra- and artificial stimulant-free composition for promoting energy in warm-blooded animals. Specifically, an ephedra- and artificial stimulant-free energy promoting composition can comprise effective amounts of a magnesium amino acid chelate, a B vitamin, a pyruvate salt, and rhodiola. The composition can further comprise a second amino acid chelate selected from the group consisting of iron amino acid chelate, zinc amino acid chelate, copper amino acid chelate, manganese amino acid chelate, chromium amino acid chelate, and combinations thereof.

In an alternative embodiment, a method of enhancing energy in a warm-blooded animal can comprise orally administering an ephedra- and artificial stimulant-free energy promoting composition to the warm blooded animal, such as in the form of a capsule, tablet, or powder. The composition for oral administration can comprise effective amounts of a magnesium amino acid chelate, a B vitamin, a pyruvate salt, and rhodiola. The composition of administration can further include a second amino acid chelate selected from the group consisting of iron amino acid chelate, zinc amino acid chelate, copper amino acid chelate, manganese amino acid chelate, chromium amino acid chelate, and combinations thereof.

Additional features and advantages of the invention will be apparent from the detailed description that follows, which illustrates, by way of example, features of the invention.

DETAILED DESCRIPTION OF THE PREFERRED EMBODIMENT(S)

Before the present invention is disclosed and described, it is to be understood that this invention is not limited to the particular process steps and materials disclosed herein because such process steps and materials may vary somewhat. It is also to be understood that the terminology used herein is used for the purpose of describing particular embodiments only. The terms are not intended to be limiting because the scope of the present invention is intended to be limited only by the appended claims and equivalents thereof.

It must be noted that, as used in this specification and the appended claims, the singular forms "a," "an," and "the" include plural referents unless the content clearly dictates otherwise.

The term "amino acid chelate" is meant to include metal ions bonded to amino acids or proteinaceous ligands forming heterocyclic rings. The bonds may be coordinate covalent, covalent, and/or ionic at the carboxyl oxygen group. However, at the amino group, the bond is typically a coordinate covalent bond. Additionally, the term "amino acid chelate" includes compositions having a traditional amino acid(s) chelated to a metal ion, and can further include other compositions chelated or complexed to the amino acid chelate. Further, the term "amino acid chelate" includes not only metals chelated to the naturally occurring amino acids, but can also include metals chelated to modified amino acids, such as creatine.

The term "B vitamin" includes folic acid, Vitamin $B_1$, Vitamin $B_2$, Vitamin $B_3$, Vitamin $B_5$, Vitamin $B_6$, or Vitamin $B_{12}$.

"*Rhodiola*" includes *Tibetan Rhodiola, Rhodiola Sacra,* or *Rhodiola Rosea* in either its native or botanical extract form.

"Coenzyme" refers to organic compounds that combine with apoenzymes to form active enzymes.

The term "cofactor" includes coenzymes and metals that are required for an enzyme to be active.

"Serving" or "single serving" is defined as a single dose, which can be orally administered in the form of a single tablet or capsule, or in the form of multiple tablets or capsules.

With these definitions in mind, an ephedra- and artificial stimulant-free energy generating composition is disclosed that can comprise effective amounts of a magnesium amino acid chelate, a B vitamin, a pyruvate salt, and rhodiola. The composition can further comprise a second amino acid chelate, such as one or more selected from the group consisting of iron amino acid chelate, zinc amino acid chelate, copper amino acid chelate, manganese amino acid chelate, and/or chromium amino acid chelate.

In an alternative embodiment, a method of enhancing energy in a warm-blooded animal can comprise orally administering an ephedra- and artificial stimulant-free energy promoting composition to a warm blooded animal. Such a composition can comprise effective amounts of a magnesium amino acid chelate, a B vitamin, a pyruvate salt, and rhodiola. Again, the composition of the method can further comprise a second amino acid chelate, such as one or more of iron amino acid chelate, zinc amino acid chelate, copper amino acid chelate, manganese amino acid chelate, and/or chromium amino acid chelate.

With respect to the blend of amino acid chelates that can be used in the compositions or methods, in one embodiment, the magnesium amino acid chelate can include multiple magnesium amino acid chelates blended together in a single serving at from 100 mg to 600 mg of magnesium. "Multiple magnesium amino acid chelates" can refer to the use of different amino acids or derivatives and/or different amino acid to metal ratios. Additional amino acid chelates can also be present to form a blend of various metals in the form of amino acid chelates. Such a blend of amino acid chelates can include an iron amino acid chelate present in a single serving at from 1 mg to 20 mg of iron, a zinc amino acid chelate present in a single serving at from 1 mg to 30 mg of zinc, a copper amino acid chelate present in a single serving at from 1 mg to 10 mg of copper, a manganese amino acid chelate present in a single serving at from 1 mg to 10 mg of manganese, and/or a chromium amino acid chelate present in a single serving at from 50 mcg to 250 mcg of chromium.

Amino acid chelates are generally produced by the reaction between amino acids and metal ions having a valence of two or more to form a heterocyclic ring structure. In such a reaction, the positive electrical charge of the metal ion is, at least partially, neutralized by the electrons available through the carboxylate or free amino groups of the amino acid.

Traditionally, the term "chelate" has been loosely defined as a combination of a metallic ion bonded to one or more ligands forming heterocyclic ring structures. Under this definition, chelate formation through neutralization of the positive charges of the divalent metal ions may be through the formation of ionic, covalent or coordinate covalent bonding. An alternative and more modern definition of the term "chelate" requires that the metal ion be bonded to the ligand solely by coordinate covalent bonds forming a heterocyclic ring. In either case, both definitions describe a metal ion and a ligand forming a heterocyclic ring.

An amino acid chelate, when properly formed, is a stable product having one or more five-membered rings formed by a reaction between the amino acid and the metal. Specifically, the carboxyl oxygen and the α-amino group of the amino acid each bond with the metal ion. Such a five-membered ring is defined by the metal atom, the carboxyl oxygen, the carbonyl carbon, the α-carbon and the α-amino nitrogen. The actual structure can depend upon the ligand to metal mole ratio and whether the carboxyl oxygen forms a coordinate covalent bond or an ionic bond with the metal ion. Generally, the ligand to metal molar ratio is at least 1:1, and is preferably 2:1 or 3:1. However, in certain instances, the ratio may be 4:1. Most typically, an amino acid chelate may be represented at a ligand to metal molar ratio of 2:1 according to Formula 1 as follows:

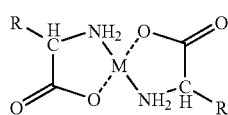

Formula 1

In the above formula, the dashed lines represent coordinate covalent bonds, covalent bonds, or ionic bonds. Further, when R is H, the amino acid is glycine, which is the simplest of the α-amino acids. However, R could be representative of any other side chain resulting in any of the other twenty or so naturally occurring amino acids derived from proteins. All of the amino acids have the same configuration for the positioning of the carboxyl oxygen and the α-amino nitrogen with respect to the metal ion. In other words, the chelate ring is defined by the same atoms in each instance, even though the R side chain group may vary. Though an amino acid to metal molar ratio of 2:1 is shown in Formula 1, this is provided by way of example only. Other compositions can also be considered amino acid chelates, as long as a metal is chelated by at least one amino acid or modified amino acid ligand. An example of a modified glycine amino acid ligand is creatine, where the two hydrogen ions of the amino group are substituted with a methyl group and a —C═NH(NH$_2$), respectively.

The structure, chemistry, and bioavailability of amino acid chelates is well documented. Patents describing such amino acid chelates include U.S. Pat. Nos. 4,020,158; 4,167,564; 4,216,143; 4,216,144; 4,599,152; 4,774,089; 4,830,716; 4,863,898; 4,725,427; 5,888,553; 5,882,685; and 6,114,379; all of which are incorporated herein, in their entireties, by reference.

One advantage of amino acid chelates in the field of mineral nutrition is attributed to the fact that these chelates are readily absorbed from the gut into mucosal cells by means of active transport. In other words, the minerals can be absorbed along with the amino acids as a single unit utilizing the amino acids as carrier molecules. Therefore, the problems associated with the competition of ions for active sites and the suppression of specific nutritive mineral elements by others can be avoided. This is especially true for compounds such as metal sulfates that are typically delivered in relatively large quantities in order for the body to absorb an appropriate amount. This is significant because large quantities often cause nausea and other discomforts as well as create an undesirable taste.

Though amino acid chelates are described above with respect to compositions containing metals and amino acids alone, it is notable that other moieties can be attached to these chelate compositions. For example, an amino acid can be chelated to a metal, and the metal can further be complexed to another amino acid or non-amino acid composition. An example of such a composition is a metal glycyl glutamine.

Magnesium amino acid chelates are included in the composition and method of the present invention. Magnesium is known to be important to the body's production of ATP. By incorporating magnesium in one or more chelate composition, the bioavailability of magnesium can be increased, thereby improving its energy providing ability. As stated, in one embodiment, one or more magnesium amino acid chelate can be present in the composition at from 100 mg to 600 mg of magnesium per serving. To be clear, a serving can consist of a single or multiple tablet(s), capsule(s), or powder(s).

Other metals can also be included in the energy producing formulations to provide enhanced energy. Again, by including these other metals as part of an amino acid chelate(s), improved bioavailability can be achieved. Examples of such metals that can be used include vanadium, iron, zinc, copper, manganese, and/or chromium. In further detail, though glycine is an amino acid that is commonly used to chelate metals, other amino acids can also be preferred for use. Other preferred naturally occurring amino acids that can be used include alanine, arginine, asparagine, aspartic acid, cysteine, cystine, glutamine, glutamic acid, glycine, histidine, hydroxyproline, isoleucine, leucine, lysine, methionine, ornithine, phenylalanine, proline, serine, threonine, tryptophan, tyrosine, valine, and combinations thereof. However, ligands including dipeptides, tripeptides, and tetrapeptides formed by any combination of the aforementioned amino acids can also be used. Further, as stated, other ligands that include an amine group and an acid group can be used, such as creatine.

Many vitamins that are commonly present in nutritional supplements can be included in the energy generating formulations. However, preferred vitamins for use include those that provide energy to the body, particularly when administered in combination with the balance of the composition of the present invention. With respect to the blend of vitamins that can be present in the compositions and methods of the present invention, vitamins for inclusion can include multiple B vitamins. In one embodiment, at least one member selected from the group consisting of folic acid, Vitamin $B_1$, Vitamin $B_2$, Vitamin $B_3$, Vitamin $B_5$, Vitamin $B_6$, and Vitamin $B_{12}$ can be present.

Thiamin, also known as Vitamin $B_1$, is derived from a substituted pyrimidine and a thiazole, which are coupled by a methylene bridge and can be used in the compositions and methods of the present invention. When thiamin is utilized in the formulation, magnesium, zinc and pyruvic acid can also be included. Thiamin can be rapidly converted to its active form, thiamin pyrophosphate (TPP), in the brain and liver by the specific enzyme, thiamin diphosphotransferase. The conversion of thiamin to TPP may be assisted by the presence of magnesium. Thiamin plays a metabolic role in the cellular production of energy, mainly in glucose metabolism, by helping to convert carbohydrates to fat for storage of potential energy. Additionally, thiamin is a cofactor in the transkelotase enzyme. Transkelotase, an enzyme which assists in the metabolism of glucose, may be activated by zinc and magnesium. Thiamin and pyruvic acid decrease the buildup of carbon dioxide in cells, a situation believed to block energy, and is involved in the conversion of pyruvic acid to acetyl-COA.

Another vitamin that can be included is cobalamin, which is more commonly known as Vitamin $B_{12}$. When Vitamin $B_{12}$ is present in the vitamin formulation, manganese, riboflavin and niacin can also be included. This vitamin may stimulate the utilization of protein, fats, and/or carbohydrates. Vitamin $B_{12}$ comprises a complex tetrapyrrol ring structure (corrin ring) and a cobalt ion in the center. Vitamin $B_{12}$ is typically synthesized by microorganisms and found in the liver of animals bound to protein as methycobalamin or 5'-deoxyadenosylcobalamin. Once the vitamin is hydrolyzed from protein, it can become active for use in the body.

Folic acid, which is a water-soluble form of Vitamin B, is a conjugated molecule consisting of a pteridine ring structure linked to para-aminobenzoic acid (PABA) that forms pteroic acid. When folic acid is present in the vitamin formulation, zinc may also be included. In combination with Vitamin $B_{12}$, folic acid can combat fatigue. Mammals generally cannot synthesize para-aminobenzoic acid, nor attach glutamate residues to pteroic acid. Thus, folate intake in the diet is required. Folic acid can be present at from 100 mcg to 400 mcg per single serving.

Niacin (nicotinic acid and nicotinamide), also known as Vitamin $B_3$, can also be used. When niacin is utilized in the vitamin formulation, potassium, magnesium, manganese, and/or chromium can also be included. Niacin acts as part of two coenzymes, nicotinamide adenine dinucleotide (NAD) and nicotinamide adenine dinucleotide phosphate (NADP), which play roles in the energy producing glycolysis cycle. Niacin can help increase energy through improving the utilization of food. Additionally, niacin in the form of nicotinic acid, can help regulate blood sugar levels as part of the glucose tolerance factor, and can be assisted by the presence of chromium, magnesium, and/or manganese. Both nicotinic acid and nicotinamide can serve as the dietary source of Vitamin $B_3$.

Pantothenic acid, also known as Vitamin $B_5$ can also be present, and can also be used with copper and/or magnesium. Pantothenic acid is formed from alanine and pantoic acid. Pantothenate is required for synthesis of coenzyme A, which is a component of the acyl carrier protein (ACP) domain of fatty acid synthase. Pantothenate may, therefore, be involved in the Krebs cycle to metabolize carbohydrates, fats, and proteins into energy.

Riboflavin, which is also known as Vitamin $B_2$, is also an optional component of the vitamin blend as well. When riboflavin is utilized in the vitamin formulation, magnesium and/or potassium can also be included. Riboflavin is a precursor for two coenzymes used in energy production, flavin mononucleotide (FMN) and flavin adenine dinucleotide (FAD). FMN and FAD may be activated by magnesium, facilitating a release of energy from glucose, fatty acids, and amino acids within mitochondria. Potassium can assist these two coenzymes in acting as hydrogen carriers to metabolize carbohydrates and fats to ATP.

Pyridoxal, pyridoxamine, and pyridoxine are collectively known as Vitamin $B_6$, and when present in the vitamin formulation, can also be accompanied by zinc, magnesium, and/or riboflavin. All three compounds can be efficiently converted to the biologically active form of Vitamin $B_6$, pyridoxal phosphate, a reaction catalyzed by the ATP requiring enzyme, pyridoxal kinase. Vitamin $B_6$ can be present in the utilization of food sources for energy, and can facilitate the release of glycogen from the liver and muscles. Vitamin $B_6$, in the form of pyridoxal phosphate, can function as a coenzyme for protein over and above the needs for growth, and can be used as a source of energy. Additionally, vitamin $B_6$ can be a cofactor of aminotransferase, an enzyme involved in energy metabolism.

Though each of these vitamins provide very specific functions in the body related to energy, many various combinations of the vitamins can work together to promote energy or prevent energy loss. Many of these vitamins participate in production of ATP, work with amino acids in body systems, and providing essential ingredients to the glycogen cycle. The B vitamin can also be supplement by a blend of essential vitamins including folic acid at from 100 mcg to 400 mcg, and/or other B vitamins which are collectively present in single serving at from 5 mg to 200 mg.

In addition to the amino acid chelates and essential vitamins that are included in the formulations of the present invention, certain complexes can also be present. For example, potassium aspartate can be present. As potassium is a monovalent ion, complexation between potassium and aspartic acid makes chelation less practical. Thus, a complex of potassium aspartate can be used in the composition of the present invention. Aspartic acid functions as a natural transport mechanism for each mineral to provide optimum absorption and efficient utilization.

Additionally, carnitine can be included in a complex form, such as L-carnitine fumarate. When L-caratine is present as part of the formulation, iron can also be included. L-carnitine has demonstrated the ability to promote oxygenation of heart muscle, support cardiovascular energy, enhance endurance training, and maintain healthy cholesterol metabolism. Fumarate, or fumaric acid, is a compound that is also naturally present in the body. As a component of the Krebs cycle (Citric Acid Cycle), fumaric acid plays a key role in generating energy. L-carnitine fumarate, thus, provides dual support for energizing the heart and muscles, unlike many other forms of carnitine. Also, L-caratine can assist in transporting long-chain fatty acids into mitochondria where they are metabolized to provide energy.

An example of a coenzyme that can be used includes coenzyme Q10, which can be accompanied by magnesium, niacin, folacin, $B_{12}$, pyridoxine, and/or pantothenic acid. Coenzyme Q10 is a compound which is abundant in cells, particularly in mitochondria, and assists in the production of ATP in the electron transport chain. Coenzyme Q10, or ubiquinone, can have a positive impact on cells of the body, and can provide enhanced energy, as well as help fight a variety of diseases. This coenzyme is believed to be present in every cell of the human body.

Biotin is another composition that can be present in the formulations of the present invention, and it may be accompanied by potassium, manganese, magnesium, and/or cobalt ($B_{12}$). Biotin is the cofactor required of enzymes that are involved in carboxylation reactions, e.g. acetyl-CoA carboxylase and pyruvate carboxylase. Biotin is found in numerous foods and also is synthesized by intestinal bacteria. Biotin can also contribute to energy production through reaction with ATP.

The pyruvate salt can be any functional salt of pyruvate, such as calcium pyruvate. The pyruvate salt can be present in a single serving at from 100 mg to 400 mg, and may be accompanied by potassium, manganese, magnesium, and/or biotin. Some of the benefits found in studies of pyruvate supplementation include increased energy, increased metabolism, increased endurance, reduced bodyfat, reduced appetite, reduced fatigue, and reduced LDL cholesterol. Pyruvate is a metabolite, i.e., a component in the metabolic system whereby glucose (blood sugar) is transformed into energy. Pyruvate functions at the cellular level, increasing the body's ability to produce energy. This energy production forces the cells to burn more glucose which allows the body to convert fat into energy. Pyruvate salt, such as calcium pyruvate, can be present in the formulation at from 200 to 400 mg per serving.

*Rhodiola* is a generic herbal term that includes *Tibetan Rhodiola, Rhodiola Sacra,* and *Rhodiola Rosea*. *Rhodiola* can be derived from a perennial plant with red, pink, or yellowish flowers. When *Rhodiola* is present in a formulation in accordance with embodiments of the present invention, magnesium can also be included. In the body, rhodiola, particularly *Rhodiola Rosea,* has been reported to reduce levels of cortisol, which triggers stress, as is helps cells synthesize triphosphate, an aid in the production of energy. *Rhodiola* extracts have been found to enhance mental and physical performance, and reportedly protect against long-term burnout and exhaustion. *Rhodiola* can improve the nervous system and mental functions such as memory, by increasing blood-supply to the muscles and brain, and it also increases protein synthesis. In one embodiment, the rhodiola used can be an extract of *Rhodiola Rosea,* and can be present in a single serving at from 50 mg to 250 mg.

In addition to these ingredients, other compositions can also be present, including other enzymes, phytonutrients, herbs, or the like.

As many of the components present in the compositions and methods of the present invention take time to generate and utilize source of energy to act on, a sugar can be present with the composition in one of many forms. For example, the sugar can be on the tablet, coated on microencapsulate core ingredients within the capsule, blended with core ingredient within the capsule, or blended with the powder form of the composition. The sugar can act to generate more instant energy while the ingredients are given time to generate energy from other sources.

The following example illustrates an aspect of the present invention. The following example should not be considered to limit the invention, but merely teaches how to make the best known energy supplement composition at the present time.

EXAMPLES

The following examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. The appended claims are intended to cover such modifications and arrangements. Thus, while the present invention has been described above with particularity, the following Examples provide further detail in connection with what are presently deemed to be the most practical and preferred embodiments of the invention.

Example 1

An ephedra- and artificial stimulant-free energy supplement was prepared and formed into tablets. A single serving is calculated based upon four (4) tablets. Table 1 below sets forth ingredients included in the formulation, as follows:

TABLE 1

| Ingredient | Amount Per Serving | % Daily Value |
|---|---|---|
| Thiamin (Vitamin $B_1$) | 1.5 mg | 100% |
| Riboflavin (Vitamin $B_2$) | 1.6 mg | 94% |
| Niacin (Niacinamide or Vitamin $B_3$) | 15 mg | 75% |
| Pyridoxine HCL (Vitamin $B_6$) | 2 mg | 100% |
| Folic Acid | 200 mcg | 50% |
| Cyanocobalamin (Vitamin $B_{12}$) | 2.4 mcg | 40% |
| Biotin | 15 mcg | 5% |
| Panthotheric Acid (D-calcium pantothenate) | 6 mg | 60% |
| Iron (amino acid chelate) | 5 mg | 28% |
| Magnesium (amino acid chelates) | 400 mg | 75% |
| Zinc (amino acid chelate) | 5 mg | 33% |
| Copper (amino acid chelate) | 3 mg | 150% |
| Chromium (amino acid chelate) | 100 mcg | 83% |
| Manganese (amino acid chelate) | 3 mg | — |
| Potassium (asparate amino acid complex) | 99 mg | 3% |
| Vanadium (amino acid chelate) | 50 mcg | — |
| Coenzyme Q10 | 10 mg | — |
| Pyruvate (calcium) | 300 mg | — |
| L-caritine fumarate | 100 mg | — |
| Rhodiola (Rhodiola rosea) | 100 mg | — |

Single serving = 4 tablets

Though the above formulation describes specific amounts of ingredients per single serving, it is understood that not all ingredients shown are necessarily essential. Further, each amount shown per ingredient can be modified to similar functional amounts to reach similar results. For example, by doubling the amount per single serving, or decreasing the amount per single serving by half, similar results may be achieved. To illustrate, 10 mg of coenzyme Q10 can be present at from 5 mg to 20 mg, though this suggested range is not included to be limiting. Such a range is merely a guideline of modification that can occur to achieve a desired result.

Other ingredients that can be present include binders and/or nominal amounts of active ingredients. Examples of such other ingredients include hydorxypropylcellulose, stearic acid, malto dextrin, croscarmellose sodium, microcrystalline cellulose, magnesium stearate, and the like. The amino acid chelates that can be used are described in U.S. Pat. Nos. 5,888,553; 5,882,685; 6,114,379; 4,599,152; and 4,830,716, which were previously incorporated herein by reference.

Example 2

Fifty individuals at various stages of life (from about 18 to 70 years) were asked to take one serving (4 tablets) of a formula described in Example 1 each time they felt tired during the daytime for a period of one month. Some of the fifty individuals commonly required daily naps, some worked in hard labor environments, some were college students, and some were mothers with many children, for example. Forty-nine of the fifty individuals reported a significant increase in their energy each time they took the product without any side effects. None reported shakiness, buzz, or nervous feelings while using the product. The individuals were able to eliminate caffeine from their diet, experience increased mental alertness and concentration, and eliminated of the need for daily naps, as applicable to each party. Night time sleep was not affected by the formula. Additionally, none experienced energy crashes in-between product usage. The fiftieth person said there was no noticeable difference in energy, but indicated that less than the recommended dose was taken.

While the invention has been described with reference to certain preferred embodiments, those skilled in the art will appreciate that various modifications, changes, omissions, and substitutions can be made without departing from the spirit of the invention. It is therefore intended that the invention be limited only by the scope of the appended claims.

What is claimed is:

1. A tablet formulation comprising a single serving of an effective amount of an ephedra- and artificial stimulant-free energy generating composition for enhancing energy in a warm-blooded animal, comprising:
    (a) a magnesium amino acid chelate;
    (b) an iron amino acid chelate
    (c) a zinc amino acid chelate
    (d) a copper amino acid chelate
    (e) a manganese amino acid chelate
    (f) a chromium amino acid chelate
    (g) a vanadium amino acid chelate
    (h) a potassium aspartate amino acid complex
    (i) folic acid
    (k) coenzyme Q10
    (l) L-carnitine fumarate
    (m) a B vitamin;
    (n) a pyruvate salt; and
    (o) rhodiola.

2. A tablet composition as in claim 1, wherein the magnesium amino acid chelate includes multiple magnesium amino acid chelates, said multiple magnesium amino acid chelates being present in a single serving at from 100 mg to 600 mg magnesium.

3. A tablet composition as in claim 1, wherein the iron amino acid chelate is present in a single serving at from 1 mg to 20 mg iron.

4. A tablet composition as in claim 1, wherein the zinc amino acid chelate is present in a single serving at from 1 mg to 30 mg zinc.

5. A tablet composition as in claim 1, wherein the copper amino acid chelate is present in a single serving at from 1 mg to 10 mg copper.

6. A table composition as in claim 1, wherein the manganese amino acid is chelate present in a single serving at from 1 mg to 10 mg manganese.

7. A tablet composition as in claim 1, wherein the chromium amino acid chelate is present in a single serving at from 50 mcg to 250 mcg chromium.

8. A tablet composition as in claim 1, wherein the composition includes multiple B vitamins selected from the group consisting of Vitamin $B_1$, Vitamin $B_2$, Vitamin $B_3$, Vitamin $B_5$, Vitamin $B_6$, and Vitamin $B_{12}$.

9. A tablet composition as in claim 1, wherein the rhodiola is an extract of *Rhodiola Rosea*, and is present in a single serving at from 50 mg to 250 mg.

10. A tablet composition as in claim 1, wherein the pyruvate salt is calcium pyruvate, and is present in a single serving at from 100 mg to 400 mg.

11. A method of enhancing energy in a warm-blooded animal, comprising orally administering a tablet formulation comprising a single serving of an effective amount of an ephedra- and artificial stimulant-free energy generating composition to a warm blooded animal, said composition comprising
    (a) a magnesium amino acid chelate;
    (b) an iron amino acid chelate
    (c) a zinc amino acid chelate
    (d) a copper amino acid chelate
    (e) a manganese amino acid chelate
    (f) a chromium amino acid chelate
    (g) a vanadium amino acid chelate
    (h) a potassium aspartate amino acid complex
    (i) folic acid
    (j) biotin
    (k) coenzyme Q10
    (l) L-carnitine fumarate
    (m) a B vitamin;
    (n) a pyruvate salt; and
    (o) rhodiola.

12. A method as in claim 11, wherein the magnesium amino acid chelate includes multiple magnesium amino acid chelates, said multiple magnesium amino acid chelates being present in a single serving at from 100 mg to 600 mg magnesium.

13. A method as in claim 11, wherein the iron amino acid chelate is present in a single serving at from 1 mg to 20 mg iron.

14. A method as in claim 11, wherein the zinc amino acid chelate is present in a single serving at from 1 mg to 30 mg zinc.

15. A method as in claim 11, wherein the copper amino acid chelate is present in a single serving at from 1 mg to 10 mg copper.

16. A method as in claim 11, wherein the manganese amino acid is chelate present in a single serving at from 1 mg to 10 mg manganese.

17. A method as in claim 11, wherein the chromium amino acid chelate is present in a single serving at from 50 mcg to 250 mcg chromium.

18. A method as in claim 11, wherein the composition includes multiple B vitamins selected from the group consisting of Vitamin $B_1$, Vitamin $B_2$, Vitamin $B_3$, Vitamin $B_5$, Vitamin $B_6$, and Vitamin $B_{12}$.

19. A method as in claim 11, wherein the rhodiola is an extract of *Rhodiola Rosea*, and is present in a single serving at from 50 mg to 250 mg.

20. A method as in claim 11, wherein the pyruvate salt is calcium pyruvate, and is present in a single serving at from 100 mg to 400 mg.

* * * * *